United States Patent
Tanaka et al.

(10) Patent No.: US 9,284,393 B2
(45) Date of Patent: Mar. 15, 2016

(54) BIOMOLECULE-COMPATIBLE, HIGHLY BRANCHED POLYMER AND BIOMOLECULAR-RECOGNITION SURFACE

(71) Applicants: KYUSHU UNIVERSITY, Fukuoka-shi, Fukuoka (JP); NISSAN CHEMICAL INDUSTRIES, LTD., Tokyo (JP)

(72) Inventors: Keiji Tanaka, Fukuoka (JP); Tomoyasu Hirai, Fukuoka (JP); Kazutaka Shimafuji, Fukuoka (JP); Masayuki Haraguchi, Funabashi (JP); Motonobu Matsuyama, Funabashi (JP)

(73) Assignees: KYUSHU UNIVERSITY, Fukuoka (JP); NISSAN CHEMICAL INDUSTRIES, LTD., Tokyo (JP)

(*) Notice: Subject to any disclaimer, the term of this patent is extended or adjusted under 35 U.S.C. 154(b) by 0 days.

(21) Appl. No.: 14/409,912

(22) PCT Filed: Jun. 24, 2013

(86) PCT No.: PCT/JP2013/067244
§ 371 (c)(1),
(2) Date: Feb. 26, 2015

(87) PCT Pub. No.: WO2013/191294
PCT Pub. Date: Dec. 27, 2013

(65) Prior Publication Data
US 2015/0299349 A1    Oct. 22, 2015

(30) Foreign Application Priority Data
Jun. 22, 2012 (JP) .................... 2012-140875

(51) Int. Cl.
| | |
|---|---|
| C08F 122/10 | (2006.01) |
| G01N 33/50 | (2006.01) |
| B05D 1/00 | (2006.01) |
| B05D 3/00 | (2006.01) |
| C09D 135/02 | (2006.01) |
| C08F 2/00 | (2006.01) |
| G01N 33/547 | (2006.01) |

(52) U.S. Cl.
CPC ............ C08F 122/105 (2013.01); B05D 1/005 (2013.01); B05D 3/007 (2013.01); C09D 135/02 (2013.01); G01N 33/547 (2013.01); *B01J 2219/0074* (2013.01); *B01J 2219/00626* (2013.01); *B01J 2219/00637* (2013.01); *B01J 2219/00722* (2013.01); *B01J 2219/00725* (2013.01)

(58) Field of Classification Search
CPC .......... C08F 122/105; C08F 2/00; C08F 4/04; C08F 22/26; C08F 12/34; G01N 33/547; B05D 1/005; B05D 3/007; C09D 135/02; B01J 2219/00626; B01J 2219/00637; B01J 2219/00722; B01J 2219/00725
USPC ............. 524/558; 526/215, 323.1, 336, 218.1
See application file for complete search history.

(56) References Cited

U.S. PATENT DOCUMENTS

| | | | | |
|---|---|---|---|---|
| 8,466,241 | B2* | 6/2013 | Haraguchi | C08F 2/00 526/215 |
| 8,773,745 | B2* | 7/2014 | Nagamura | C08F 8/30 252/586 |
| 2011/0149367 | A1* | 6/2011 | Nagamura | C08F 8/30 359/265 |
| 2012/0059136 | A1* | 3/2012 | Haraguchi | C08F 2/00 526/215 |

FOREIGN PATENT DOCUMENTS

| | | |
|---|---|---|
| JP | H11-148934 A | 6/1999 |
| JP | H11-332595 A | 12/1999 |
| JP | 2004-531390 A | 10/2004 |
| JP | 2009-139112 A | 6/2009 |
| JP | 2010-189525 A | 9/2010 |
| JP | 2010189525 A * | 9/2010 |
| WO | 2009/136626 A1 | 11/2009 |
| WO | 2010/126140 A1 | 11/2010 |

OTHER PUBLICATIONS

Sep. 24, 2013 International Search Report issued in Application No. PCT/JP2013/067244.
Sep. 24, 2013 Written Opinion issued in International Application No. PCT/JP2013/067244.

* cited by examiner

*Primary Examiner* — Michael M Bernshteyn
(74) *Attorney, Agent, or Firm* — Oliff PLC

(57) ABSTRACT

A biomolecule-compatible highly branched polymer obtained by polymerizing a monomer having an alkylene oxide and two or more radically polymerizable double bonds in a molecule in presence of a polymerization initiator in 5 mol % or more and 200 mol % or less relative to the moles of monomer, wherein molecular terminals of biomolecule-compatible highly branched polymer have one biomolecular site of at least one pair from the group of combination pairs of biotin and avidin, an antigen and antibody, polynucleotide and polynucleotide having complementary base sequence thereof, cDNA and mRNA, enzyme and substrate, an enzyme and product, an enzyme and competitive inhibitor, an enzyme (binding site) and coenzyme, an enzyme (binding site) and triazine dye, protease and protease inhibitor, Fc site and protein A, Fc site and protein G, lectin and sugar, hormone receptor and hormone, DNA and DNA binding protein, heparin and fibronectin, and heparin and laminin.

16 Claims, 3 Drawing Sheets

BIOMOLECULE-COMPATIBLE, HIGHLY BRANCHED POLYMER AND BIOMOLECULAR-RECOGNITION SURFACE

TECHNICAL FIELD

The present invention relates to a biomolecule-compatible highly branched polymer and a surface (a film) having a biomolecular-recognition function and formed by using the biomolecule-compatible highly branched polymer.

BACKGROUND ART

In recent years, polymer (macromolecule) materials have been increasingly used in various fields. As the materials are increasingly used, the characteristics of a surface or an interface of the polymer as well as polymer properties as a matrix have been important for polymer materials according to the fields. In particular, in recent years, polymer materials capable of forming a polymer surface that can recognize biomolecules such as DNA, proteins, and cells are expected to be applied to micro-total analysis systems (μ-TAS), microarrays, SPR chips, and personalized medical treatment.

DNA chips used for analyzing the base sequence of DNA or DNA fragments are detection tools made by fixing a large number of DNA or a large number of DNA fragments or nucleotide derivatives such as synthetic oligonucleotides, as molecules of DNA detection (probe molecules) on the surface of a solid-phase substrate. Representative DNA chips are microarrays in which a large number of probe molecules are aligned and fixed on a solid-phase carrier such as a slide glass. With the advent of the DNA chips, expression, mutation, polymorphism, and the like of genes have been able to be efficiently examined in a short period. However, a technique for aligning a large number of DNA fragments or oligonucleotides on the surface of the solid-phase substrate in high density and in a stable state is required for fabrication of the DNA chip.

In Patent Document 1, a measurement chip made by fixing peptide nucleic acid (PNA) on a solid-phase substrate through covalent bonds is disclosed. In Patent Document 1, an example of producing the measurement chip on which a molecular-recognition surface made by fixing avidin as a probe molecule is produced is disclosed. The molecular-recognition surface is formed by a method of immersing a glass substrate on which a metal such as chromium and gold has been vapor-deposited into an ethanol solution of 11-mercaptoundecanoic acid having a thiol group for 24 hours to form an organic thin film layer on the metal vapor deposited layer and thereafter adding an avidin solution dropwise onto the thin film layer. The avidin-fixed surface recognizes PNA having biotin and fixes PNA. The DNA fragment bonded and fixed to PNA through hybridization is detected by using a surface plasmon resonance phenomenon.

In Patent Document 2, a method of preparing a molecular-recognition surface as a biotin recognition surface on which biotin as a molecular probe is fixed on a substrate is disclosed. The molecular-recognition surface is formed by applying a solution of a compound containing silane, poly(ethylene oxide), and biotin as reactive sites with the substrate onto the substrate such as a silicon wafer, glass, or polystyrene for a culture substrate by spin coating.

PRIOR ART DOCUMENTS

Patent Documents

Patent Document 1: Japanese Patent Application Publication No. H11-332595 (JP H11-332595 A)

Patent Document 2: Japanese Unexamined Patent Application Publication No. 2004-531390 (JP 2004-531390 T)

SUMMARY OF THE INVENTION

Problem to be Solved by the Invention

For the production of the measurement chip described in Patent Document 1, a thiol and avidin need to be fixed stepwise on a glass substrate having a metal vapor deposited film and, in addition, the glass substrate needs to be immersed in a thiol solution for 24 hours for fixing the thiol onto the metal vapor deposited film. The method for producing the molecular-recognition surface needs much time and much labor and thus this method is inefficient.

In Patent Document 2, the molecular-recognition surface can be formed relatively in a short period by applying the solution of the compounds containing silane, polyethylene oxide, and biotin onto the substrate by spin coating. However, avidin can be fixed only onto substrates having a silanol part such as a silicon wafer and glass that can react with a silane part in the compounds. Therefore, fixing the compounds disclosed in Patent Document 2 onto a plastic substrate such as polystyrene, which is low price and light weight, requires a process of applying plasma treatment and the like to the surface of polystyrene to generate hydroxy groups in advance, which limits freedom of substrate selection.

Means for Solving the Problem

As a result of intensive studies to achieve the above objects, the inventors of the present invention have found that a molecular-recognition surface can be easily formed on various substrates such as plastics by a method of applying a resin blend containing a highly branched polymer having biomolecular sites and a low hydrophilic thermoplastic resin by spin coating and other coating methods that can fabricate a thin film in a short period, and have completed the present invention.

As a first aspect, the present invention relates to a biomolecule-compatible highly branched polymer obtained by polymerizing a monomer having an alkylene oxide and two or more radically polymerizable double bonds in a molecule in the presence of a polymerization initiator in an amount of 5 mol % or more and 200 mol % or less relative to the number of moles of the monomer, in which molecular terminals of the biomolecule-compatible highly branched polymer have one biomolecular site of at least one pair selected from the group consisting of the pairs of combinations of biotin and avidin, an antigen and an antibody, a polynucleotide and a polynucleotide having a complementary base sequence of the former polynucleotide, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

As a second aspect, the present invention relates to the biomolecule-compatible highly branched polymer according to the first aspect, in which the monomer is a compound having either or both of a vinyl group and a (meth)acrylic group.

As a third aspect, the present invention relates to the biomolecule-compatible highly branched polymer according to the second aspect, in which the monomer is a divinyl compound or a di(meth)acrylate compound.

As a fourth aspect, the present invention relates to the biomolecule-compatible highly branched polymer according to the third aspect, in which the monomer is a compound of Formula [1]:

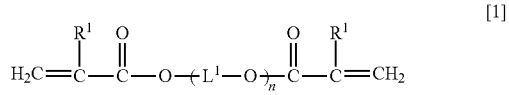

(where $R^1$ each is independently a hydrogen atom or a methyl group; $L^1$ is a $C_{2-6}$ alkylene group; and n is an integer of 1 to 30).

As a fifth aspect, the present invention relates to the biomolecule-compatible highly branched polymer according to the first aspect, in which the polymerization initiator is an azo-based polymerization initiator.

As a sixth aspect, the present invention relates to the biomolecule-compatible highly branched polymer according to the fifth aspect, in which the polymerization initiator is 4,4'-azobis(4-cyanovaleric acid).

As a seventh aspect, the present invention relates to a varnish comprising: the biomolecule-compatible highly branched polymer as described in any one of the first aspect to the sixth aspect.

As an eighth aspect, the present invention relates to a thin film fabricated from the biomolecule-compatible highly branched polymer as described in any one of the first aspect to the sixth aspect.

As a ninth aspect, the present invention relates to a resin blend comprising: (a) the biomolecule-compatible highly branched polymer as described in any one of the first aspect to the sixth aspect; and (b) a low hydrophilic thermoplastic resin.

As a tenth aspect, the present invention relates to a thin film fabricated from the resin blend as described in the ninth aspect.

As an eleventh aspect, the present invention relates to a method for producing a thin film fabricated from the biomolecule-compatible highly branched polymer as described in any one of the first aspect to the sixth aspect, the method comprising:

applying a liquid in which the biomolecule-compatible highly branched polymer is contained in a solvent onto a substrate by a spin coating method to form a coating film; and removing the solvent by drying the coating film.

As a twelfth aspect, the present invention relates to a method for producing a thin film fabricated from the resin blend as described in the ninth aspect, the method comprising:

applying a liquid in which the resin blend is contained in a solvent onto a substrate by a spin coating method to form a coating film;

removing the solvent by drying the coating film; and annealing the obtained coating film in the atmosphere of a hydrophilic medium.

As a thirteenth aspect, the present invention relates to a molecular-recognition surface chip comprising: the thin film as described in the eleventh aspect or the twelfth aspect on a substrate, in which with the thin film, the molecular-recognition surface chip is capable of recognizing one biomolecule of at least one pair selected from the group consisting of the pairs of combinations of biotin and avidin, an antigen and an antibody, a polynucleotide and a polynucleotide having a complementary base sequence of the former nucleotide, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

As a fourteenth aspect, the present invention relates to an activated carboxy group-containing highly branched polymer, obtained by causing a carboxy group-containing highly branched polymer obtained by polymerizing a monomer having an alkylene oxide and two or more radically polymerizable double bonds in a molecule, in the presence of a polymerization initiator having carboxy groups in the molecule of the polymerization initiator in an amount of 5 mol % or more and 200 mol % or less relative to the number of moles of the monomer, to react with N-hydroxysuccinimide, in which a part of or all of the carboxy groups are hydroxysuccinimide-esterified.

As a fifteenth aspect, the present invention relates to a method for producing the biomolecule-compatible highly branched polymer as described in the first aspect, the method characterized by comprising: causing the activated carboxy group-containing highly branched polymer as described in the fourteenth aspect to react with a compound having a functional group capable of reacting with the activated carboxy group and having one biomolecular site of at least one pair selected from the group consisting of the pairs of combinations of biotin and avidin, an antigen and an antibody, a polynucleotide and a polynucleotide having a complementary base sequence of the former nucleotide, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

As a sixteenth aspect, the present invention relates to the method according to the fifteenth aspect, in which the functional group capable of reacting with the activated carboxy group is an amino group.

Effects of the Invention

The highly branched polymer having biomolecular-recognition sites of the present invention can easily form a film using a varnish containing the polymer or a resin blend containing the polymer, by spin coating. In addition, with the polymer, a molecular-recognition surface can be fabricated on the substrate in a short period.

The highly branched polymer having biomolecular-recognition sites of the present invention aggressively introduces a branched structure and thus the highly branched polymer has less intermolecular entanglements than linear polymers and displays particulate-like behavior. In the matrix of a low hydrophilic thermoplastic resin, the highly branched polymer easily moves to a surface or an interface and thus tends to provide activity to the surface of the resin. Therefore, when a formed body such as a film is fabricated from the resin blend containing the highly branched polymer having biomolecular-recognition sites of the present invention and the thermoplastic resin, the particulate-like highly branched polymer can easily move to an interface (a film surface) and thus the formed body (the film) having an increased amount of the highly branched polymer present in its surface can be formed. In other words, the formed body (the film) whose surface can recognize molecules can be formed from the resin blend made by adding the low hydrophilic thermoplastic resin and the like to the highly branched polymer having biomolecular-recognition sites of the present invention.

MODES FOR CARRYING OUT THE INVENTION

<Biomolecule-Compatible Highly Branched Polymer>

Figure 1:
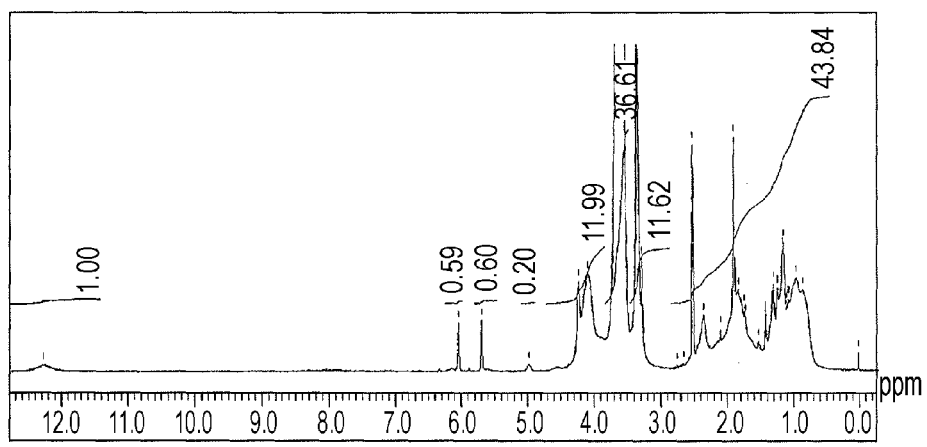
FIG. 1 is a chart showing the $^1$H NMR spectrum of Highly branched polymer 1 produced in Synthesis Example 1.

The biomolecule-compatible highly branched polymer of the present invention is a highly branched polymer obtained by polymerizing a monomer having an alkylene oxide and two or more radically polymerizable double bonds in the molecule of the monomer in the presence of a polymerization initiator in an amount of 5 mol % or more and 200 mol % or less relative to the number of moles of the monomer, in which the molecular terminals of the biomolecule-compatible highly branched polymer have one biomolecular site of a pair of complementary biomolecular sites such as biotin and avidin.

Specifically, the biomolecule-compatible highly branched polymer of the present invention is a polymer having biomolecular sites at the molecular terminals through bonding groups.

The biomolecule-compatible highly branched polymer is what is called an initiator-fragment incorporation radical polymerization (IFIRP) highly branched polymer, and has the fragments of the polymerization initiator used for the polymerization at the terminals of the polymer.

In the biomolecule-compatible highly branched polymer, multifunctional monomers and/or monofunctional monomers not included in the monomers described below may be copolymerized if necessary as long as the effect of the present invention is not impaired.

[Monomer]

The monomer having an alkylene oxide and two or more radically polymerizable double bonds in the molecule of the monomer is preferably has either or both of a vinyl group and a (meth)acrylic group and is particularly preferably a divinyl compound or a di(meth)acrylate compound. In particular, the monomer is more preferably the compound of Formula [1]. In the present invention, the (meth)acrylate compound refers to both acrylate compound and methacrylate compound. For example, (meth)acrylic acid refers to both acrylic acid and methacrylic acid.

Examples of the monomer include ethylene glycol di(meth)acrylate, diethylene glycol di(meth)acrylate, triethylene glycol di(meth)acrylate, propylene glycol di(meth)acrylate, dipropylene glycol di(meth)acrylate, tripropylene glycol di(meth)acrylate, trimethylene glycol di(meth)acrylate, tetramethylene glycol di(meth)acrylate, neopentyl glycol di(meth)acrylate, 1,6-hexanediol di(meth)acrylate, poly(ethylene glycol) (molecular weight: 200, 300, 400, 600, 1000, etc.) di(meth)acrylate, poly(propylene glycol) (molecular weight: 400, 500, 700, etc.) di(meth)acrylate, poly(tetramethylene glycol) (molecular weight: 650, etc.) di(meth)acrylate, and ethoxylated poly(propylene glycol) (molecular weight: 700, etc.) di(meth)acrylate.

Among them, polyethylene glycol di(meth)acrylate, poly(propylene glycol) di(meth)acrylate, and poly(tetramethylene glycol) di(meth)acrylate are preferable. Among them, poly(ethylene glycol) di(meth)acrylate and poly(propylene glycol) di(meth)acrylate are preferable and poly(ethylene glycol) di(meth)acrylate is more preferable.

[Polymerization Initiator]

As the polymerization initiator, an azo-based polymerization initiator is preferably used. Examples of the azo-based polymerization initiator include the following compounds of (1) to (5).

(1) Azonitrile Compounds:
2,2'-azobisisobutyronitrile, 2,2'-azobis(2-methylbutyronitrile), 2,2'-azobis(2,4-dimethylvaleronitrile), 1,1'-azobis(1-cyclohexanecarbonitrile), 2,2'-azobis(4-methoxy-2,4-dimethylvaleronitrile), 2-(carbamoylazo)isobutyronitrile, and the like;

(2) Azoamide Compounds:
2,2'-azobis{2-methyl-N-[1,1-bis(hydroxymethyl)-2-hydroxyethyl]propionamide},
2,2'-azobis{2-methyl-N-[2-(1-hydroxybutyl)]propionamide},
2,2'-azobis[2-methyl-N-(2-hydroxyethyl)propionamide],
2,2'-azobis[N-(2-propenyl)-2-methylpropionamide],
2,2'-azobis(N-butyl-2-methylpropionamide),
2,2'-azobis(N-cyclohexyl-2-methylpropionamide), and the like;

(3) Cyclic Azoamidine Compounds:
2,2'-azobis[2-(2-imidazolin-2-yl)propane]dihydrochloride,
2,2'-azobis[2-(2-imidazolin-2-yl)propane]disulfate dihydrate,
2,2'-azobis[2-[1-(2-hydroxyethyl)-2-imidazolin-2-yl]propane]dihydrochloride,
2,2'-azobis[2-(2-imidazolin-2-yl)propane],
2,2'-azobis(1-imino-1-pyrrolidino-2-methylpropane)dihydrochloride, and the like;

(4) Azoamidine Compounds:
2,2'-azobis(2-methylpropionamidine)dihydrochloride,
2,2'-azobis[N-(2-carboxyethyl)-2-methylpropionamidine] tetrahydrate, and the like; and (5) Others:
2,2'-dimethyl azobisisobutyrate, 4,4'-azobis(4-cyanovaleric acid),
2,2'-azobis(2,4,4-trimethylpentane), 1,1'-azobis(1-acetoxy-1-phenylethane), dimethyl 1,1'-azobis(1-cyclohexanecarboxylate), and the like.

Among the azo-based polymerization initiators, 4,4'-azobis(4-cyanovaleric acid) is preferable from the viewpoint of the easiness of the introduction of biomolecular sites to the terminals of the highly branched polymer described below.

The polymerization initiator is used in an amount of 5 mol % or more and 200 mol % or less, preferably used in an amount of 20 mol % or more and 200 mol % or less, and more preferably used in an amount of 20 mol % or more and 100 mol % or less relative to the number of moles of the monomer.

[Method for Producing Highly Branched Polymer]

Examples of the method of polymerizing the monomer in the presence of the polymerization initiator in the predetermined amount relative to the monomer include known methods such as solution polymerization, dispersion polymerization, precipitation polymerization, and mass polymerization. Among them, the solution polymerization or the precipitation polymerization is preferable. In particular, the reaction is preferably carried out by the solution polymerization in an organic solvent from the viewpoint of molecular weight control.

Examples of the organic solvent used in the reaction include aromatic hydrocarbons such as benzene, toluene, xylene, ethylbenzene, and tetralin; aliphatic or alicyclic hydrocarbons such as n-hexane, n-heptane, mineral spirits, and cyclohexane; halides such as methyl chloride, methyl bromide, methyl iodide, dichloromethane, chloroform, carbon tetrachloride, trichloroethylene, perchloroethylene, and o-dichlorobenzene; esters or ester ethers such as ethyl acetate, butyl acetate, methoxybutyl acetate, methyl cellosolve acetate, ethyl cellosolve acetate, and propylene glycol monomethyl ether acetate; ethers such as diethyl ether, tetrahydrofuran, 1,4-dioxane, methyl cellosolve, ethyl cellosolve, butyl cellosolve, and propylene glycol monomethyl ether; ketones such as acetone, methyl ethyl ketone, methyl isobutyl ketone, di-n-butyl ketone, and cyclohexanone; alcohols such as methanol, ethanol, n-propanol, isopropanol, n-butanol, isobutanol, tert-butanol, 2-ethylhexyl alcohol, benzyl alcohol, and ethylene glycol; amides such as N,N-dimethylformamide, N,N-dimethylacetamide, and N-methyl-2-pyrrolidone; and sulfoxides such as dimethyl sulfoxide, and mixed solvents of two or more of these solvents.

Among them, the aromatic hydrocarbons, halides, esters, ester ethers, ethers, ketones, alcohols, and amides are preferable and particularly preferable solvents include benzene, toluene, xylene, o-dichlorobenzene, ethyl acetate, butyl acetate, propylene glycol monomethyl ether acetate, propylene glycol monomethyl ether, tetrahydrofuran, 1,4-dioxane, methyl ethyl ketone, methyl isobutyl ketone, methanol, ethanol, n-propanol, isopropanol, n-butanol, isobutanol, tert-butanol, N,N-dimethylformamide, N,N-dimethylacetamide, and N-methyl-2-pyrrolidone.

When the polymerization reaction is carried out in the presence of the organic solvent, the mass of the organic solvent relative to 1 part by mass of the monomer is usually 5 to 120 parts by mass and preferably 10 to 110 parts by mass.

The polymerization reaction is usually carried out at normal pressure, under pressurized and sealed conditions, or under reduced pressure. The polymerization reaction is preferably carried out at normal pressure from the viewpoint of the simplicity of apparatus and easiness of operation. In addition, the polymerization reaction is preferably carried out in the atmosphere of an inert gas such as $N_2$.

A polymerization temperature is any temperature as long as the temperature is equal to or lower than the boiling point of the reaction mixture. The temperature is preferably 50° C. or more and 200° C. or less, further preferably 80° C. or more and 150° C. or less, and more preferably 80° C. or more and 130° C. or less from the viewpoint of polymerization efficiency and molecular weight adjustment.

A reaction time varies depending on the reaction temperature, the types and ratios of the monomer and the polymerization initiator, the polymerization solvent, and the like and thus the time may not be generally determined. The time is preferably 30 minutes or more and 720 minutes or less and more preferably 40 minutes or more and 540 minutes or less.

After the polymerization reaction is completed, the obtained highly branched polymer is recovered by any methods. Aftertreatment such as washing is carried out if necessary. Examples of the method of recovering the macromolecules from the reaction solution include a reprecipitation method.

A weight average molecular weight (Mw) of the highly branched polymer measured by gel permeation chromatography in terms of polystyrene is 1,000 to 400,000 and preferably 2,000 to 200,000.

[Bonding Group]

Any bonding groups contained in the structure of the biomolecule-compatible highly branched polymer of the present invention can be used as long as the bonding group is a bivalent organic group and can bond the functional groups of the highly branched polymer terminals and the biomolecular sites described below. Preferable examples of the bonding group include groups bonding the terminal functional groups and the biomolecular sites with groups such as ester bonds, amide bonds, ether bonds, and other bonds through which covalent bonds are easy to be formed. For example, when both of the terminal functional groups and the functional groups that the biomolecular sites have are carboxy groups or derivative of the carboxy groups, example of such bonding groups include alkylenediamino group such as hexamethylenediamino group.

[Biomolecular Site]

The biomolecular sites existing at molecular terminals of the biomolecule-compatible highly branched polymer of the present invention are one of the biomolecular sites of a pair of the complementary biomolecular sites such as biotin and avidin. Example of the pair of combinations include biotin and avidin, an antigen and an antibody, a polynucleotide and a polynucleotide having a complementary base sequence, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

The biomolecule-compatible highly branched polymer of the present invention may have either one of the pair at its molecular terminals or each one of two or more of the pairs. In these pairs, the biomolecular sites bonding to the molecular terminals of the highly branched polymer may be any one of the biomolecular sites. Among these pairs, biotin and avidin are particularly preferable.

<Method for Producing Biomolecule-Compatible Highly Branched Polymer>

The biomolecule-compatible highly branched polymer of the present invention is obtained by causing the activated carboxy group-containing highly branched polymer, which is a precursor of the biomolecule-compatible highly branched polymer of the present invention, to react with the compound that has a functional group capable of reacting with the activated carboxy group and one biomolecular site of a pair of the complementary biomolecular sites, that is, one biomolecular site of at least one pair selected from the group consisting of the pairs of combinations of biotin and avidin, an antigen and an antibody, a polynucleotide and a polynucleotide having a complementary base sequence, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

The method for producing and the activated carboxy group-containing highly branched polymer are also included in the scope of the present invention The activated carboxy group-containing highly branched polymer is a polymer obtained by causing a carboxy group-containing highly branched polymer obtained by polymerizing a monomer having an alkylene oxide and two or more radically polymerizable double bonds in the molecule, in the presence of a polymerization initiator having carboxy groups in the molecule of the polymerization initiator in an amount of 5 mol % or more and 200 mol % or less relative to the number of moles of the monomer, to react with a known activated esterification agent to carry out activated esterification to a part of or all of the carboxy groups.

Examples of the known activated esterification agent may include nitrophenol, pentafluorophenol, and N-hydroxysuccinimide.

The carboxy group-containing highly branched polymer can be produced by the method previously described in [Method for producing highly branched polymer]. As the monomer, the monomers previously described in [Monomer] can be preferably used and, as the polymerization initiator, the polymerization initiator having carboxy groups such as 4,4'-azobis(4-cyanovaleric acid) previously described in [Polymerization initiator] can be suitably used.

The reaction of the carboxy group-containing highly branched polymer and the activated esterification agent can be carried out in a solvent that can dissolve the compounds. A part of or all of the carboxy groups of the highly branched polymer are bonded to the activated esterification agent to obtain the activated carboxy group-containing highly branched polymer. Examples of the solvent include the previously described solvents used for producing the carboxy group-containing highly branched polymer.

In order to accelerate the reaction, a condensing agent is preferably used. Any of the condensing agents can be used as long as the condensing agents are a compound that can accelerate a condensation reaction with amino groups and the like by the activation of carboxylic acid. Example of the condensing agents include dicyclohexylcarbodiimide (DCC), diisopropylcarbodiimide (DIC), 1-ethyl-3-(3-dimethylaminopropyl)carbodiimide (EDC) hydrochloride, carbonyldiimidazole, triphenyl phosphite, diphenyl dichlorophosphate, and diphenyl(2,3-dihydro-2-thioxo-3-benzoxazolyl)phosphonate.

In the reaction, the activated esterification agent is used in an amount of 0.1 time to 10 times in mole relative to the amount of the carboxy group of the carboxy group-containing highly branched polymer. The ratio of the activated carboxy groups to all the carboxy groups can be adjusted by changing the amount of the activated esterification agent used.

The reaction is usually carried out at normal pressure, under pressurized and sealed conditions, or under reduced pressure. The reaction is preferably carried out at normal pressure from the viewpoint of the simplicity of apparatus and easiness of operation. In addition, the reaction is preferably carried out in the atmosphere of an inert gas such as $N_2$.

At this time, the reaction is desirably carried out at a reaction temperature of −80 to 200° C., preferably 0 to 100° C., and more preferably 10 to 50° C. and for a reaction time of 0.1 to 48 hours and preferably 0.2 to 40 hours.

After the polymerization reaction is completed, the obtained activated carboxy group-containing highly branched polymer is recovered by any methods. Aftertreatment such as washing is carried out if necessary. Examples of the method of recovering the macromolecules from the reaction solution include a reprecipitation method.

In the compound reacting with the activated carboxy group-containing highly branched polymer and having the functional group capable of reacting with the activated carboxy group and one biomolecular site of a pair of the complementary biomolecular sites, examples of the functional group capable of reacting with the activated carboxy group include a hydroxy group, a mercapto group, and an amino group and a preferable example is the amino group.

Examples of the pair of the complementary biomolecular sites include combinations of biotin and avidin, an antigen and an antibody, a polynucleotide and a polynucleotide having a complementary base sequence, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin. Among them, biotin and avidin are preferable.

Here, as the compound having the functional group capable of reacting with the activated carboxy group and one biomolecular site of a pair of the complementary biomolecular sites, commercially available products can be used or the compound can be obtained by preparing derivatives of the above biomolecules by known methods.

For the reaction of the activated carboxy group-containing highly branched polymer and the compound having the functional group capable of reacting with the activated carboxy group and one biomolecular site of a pair of the complementary biomolecular sites, known methods such as an activated esterification method used for peptide formation can be applied.

<Method for Producing Varnish and Thin Film Containing Biomolecule-Compatible Highly Branched Polymer>

A specific method for forming a thin film fabricated from the biomolecule-compatible highly branched polymer of the present invention includes dissolving or dispersing the biomolecule-compatible highly branched polymer in a solvent to form a product in the form of a varnish (a film formation material), applying the varnish onto a substrate by application methods such as a cast coating method, a spin coating method, a blade coating method, a dip coating method, a roll coating method, a bar coating method, a die coating method, a spray coating method, an inkjet method, a printing method (relief printing, intaglio printing, planographic printing, screen printing, etc.), and drying the applied film with a hot plate or an oven to form a thin film.

Among these application methods, the spin coating method is preferable. Use of the spin coating method has advantages that even a solution having high volatility can be employed because the varnish can be applied in a short period and highly uniform application can be carried out.

The solvent used in the product in the form of the varnish may be a solvent that dissolves the biomolecule-compatible highly branched polymer and examples of the solvent include methanol, acetone, tetrahydrofuran (THF), toluene, N,N-dimethylformamide (DMF), cyclohexanone, propylene glycol monomethyl ether (PGME), propylene glycol monomethyl ether acetate (PGMEA), propylene glycol monoethyl ether, ethyl lactate, diethylene glycol monoethyl ether, butyl cellosolve, and γ-butyrolactone. These solvents can be used singly or in combination of two or more of the solvents.

The concentration of the biomolecule-compatible highly branched polymer dissolved or dispersed into the solvent is any concentrations. The concentration of the biomolecule-compatible highly branched polymer is 0.01 to 90% by mass, preferably 0.05 to 50% by mass, and more preferably 0.1 to 20% by mass relative to the total mass (the sum of the mass) of the biomolecule-compatible highly branched polymer and the solvent.

The thickness of the thin film formed from the biomolecule-compatible highly branched polymer is not particularly limited. The thickness is usually 0.005 to 50 µm and preferably 0.01 to 20 µm.

<Resin Blend Containing Biomolecule-Compatible Highly Branched Polymer>

The present invention also relates to a resin blend containing the biomolecule-compatible highly branched polymer and a low hydrophilic thermoplastic resin.

[Thermoplastic Resin]

Any thermoplastic resin can be contained in the resin composition of the present invention. The thermoplastic resin is preferably a low hydrophilic thermoplastic resin. Examples of the low hydrophilic thermoplastic resin in the present invention include polyolefin-based resins such as polyethylene (PE), polypropylene (PP), ethylene-vinyl acetate copolymer (EVA), and ethylene-ethyl acrylate copolymer (EEA); polystyrene-based resins such as polystyrene (PS), high impact polystyrene (HIPS), acrylonitrile-styrene copolymer (AS), acrylonitrile-butadiene-styrene copolymer (ABS), and methyl methacrylate-styrene copolymer (MS); polycarbonate resins; vinyl chloride resins: polyamide resins; polyimide resins; (meth)acrylic resins such as poly(methyl methacrylate) (PMMA); polyester resins such as poly(ethylene terephthalate) (PET), poly(butylene terephthalate), poly(ethylene naphthalate), poly(butylene naphthalate), poly(lactic acid) (PLA), poly(3-hydroxybutyric acid), polycaprolactone, poly(butylene succinate), and poly(ethylene succinate/adipate); poly(phenylene ether) resins; modified poly(phenylene ether) resins; polyacetal resins; polysulfone resins, and a poly(phenylene sulfide) resin.

Among them, the polystyrene resins and the poly(methyl methacrylate) resins are preferable.

In the resin blend, the biomolecule-compatible highly branched polymer is preferably contained in an amount of 0.01 to 50% by mass and particularly preferably 0.1 to 40% by mass relative to the thermoplastic resin.

<Thin Film Fabricated from Resin Blend and Method for Forming the Same>

The resin blend of the present invention can be dissolved or dispersed into a solvent to be the form of a varnish (a film formation material), and then be applied onto a substrate (coating) to form a thin film and further a formed body.

Any methods for applying onto the substrate can be selected from a cast coating method, a spin coating method, a blade coating method, a dip coating method, a roll coating method, a bar coating method, a die coating method, a spray coating method, an inkjet method, a printing method (relief printing, intaglio printing, planographic printing, screen printing, etc.). Among them, the spin coating method is desirably used because the spin coating method has advantages that even a solution having high volatility can be employed because the varnish can be applied in a short period and highly uniform application can be carried out. Here, it is preferable that the resin blend be applied after filtration using a filter having a pore diameter of about 0.2 µm.

The solvent used for the product in the form of the varnish may be a solvent that dissolves the resin blend. Specific examples of the solvents include the same solvents described in <Method for producing varnish and thin film containing biomolecule-compatible highly branched polymer>.

A solid content of the varnish is, for example, 0.01 to 50% by mass, 0.05 to 30% by mass, or 0.1 to 20% by mass. Here, the solid content means components obtained by removing the solvent component from all the components of the varnish.

Examples of the substrate include a silicon/silicon dioxide coated substrate, a silicon wafer, a silicon nitride substrate, a glass substrate, an ITO substrate, a plastic substrate (polyimide, polycarbonate, polymethacrylate, polystyrene, polyester, polyolefin, epoxy, melamine, triacetyl cellulose, ABS, AS, norbornene-based resins, etc.), a metal, a wood, a paper, a glass, and a slate. The shapes of these substrates may be a plate-like shape, a film-like shape, or a three-dimensional formed body.

After application, subsequently the applied film is dried with a hot plate or an oven to remove the solvent if necessary. At this time, depending on the solvent used, a drying temperature and a drying time can be adequately selected from room temperature (about 25° C.) to 400° C. and from 10 seconds to 48 hours, respectively.

Subsequently, the obtained coating film from which the solvent has been removed is preferably annealed in the atmosphere of a hydrophilic medium. This annealing is what is called "solvent annealing".

Here, the term "solvent annealing" means solvent vapor treatment and means that the film is exposed to air containing solvent vapor at room temperature or higher temperature in a sealed container. The solvent annealing generally can change the surface state of the film. In the present invention, the amount of the biomolecule-compatible highly branched polymer present in the film surface can be further increased.

In the present invention, examples of the hydrophilic medium (the solvent used in the solvent annealing) include alcohols such as methanol and ethanol. Among them, methanol is preferable.

The temperature at the time of annealing and an annealing time (time for exposure to the solvent vapor) are not particularly limited. For example, the temperature and the time can be selected from room temperature (about 25° C.) to the boiling point of the solvent and from 10 seconds to 48 hours, respectively.

The thickness of the applied film after drying and solvent annealing is usually 0.005 to 50 µm and preferably 0.01 to 20 µm.

<Molecular-Recognition Surface Chip>

The biomolecule-compatible highly branched polymer of the present invention is suitably used as the material for the molecular-recognition surface chip, particularly used as the material for the molecular-recognition surface chip that can recognize one biomolecule of at least one pair selected from the group consisting of the pairs of combinations of biotin and avidin, an antigen and an antibody, a polynucleotide and a polynucleotide having a complementary base sequence, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

The molecular-recognition surface chip of the present invention is a chip including the thin film fabricated from the varnish of the above biomolecule-compatible highly branched polymer or the thin film fabricated from the resin blend containing the above biomolecule-compatible highly branched polymer on at least one side of the substrate.

The molecular-recognition surface chip of the present invention can be formed through a step of applying the varnish of the above biomolecule-compatible highly branched polymer onto the substrate to form a coating film and a step of drying the coating film to remove the solvent.

The molecular-recognition surface chip of the present invention also can be formed through a step of applying the resin blend (a liquid containing the resin blend in a solvent) containing the biomolecule-compatible highly branched polymer onto the substrate to form a coating film, a step of drying the coating film to remove the solvent, and a step of annealing the obtained coating film in the atmosphere of the hydrophilic medium.

As these detailed procedure, the above described <Method for producing varnish and thin film containing biomolecule-compatible highly branched polymer> and <Thin film fabricated from resin blend and method for forming the same> can be applicable.

EXAMPLES

Hereinafter, the present invention will be described in detail with reference to Synthesis Examples and Examples. However, the present invention is not limited to the following description.

(1) Gel Permeation Chromatography (GPC)
Apparatus: HLC-8220GPC, manufactured by Tosoh Corporation
Column: Shodex (registered trademark) GPC KF-804L and GPC KF-805L, manufactured by Showa Denko K.K.
Column temperature: 40° C.
Solvent: Tetrahydrofuran
Detector: RI
(2) $^1$H NMR Spectrum
Apparatus: JNM-ECA700, manufactured by JEOL Ltd. DATUM Solution Business
Operations (Synthesis Example 1)
JNM-ECP400, manufactured by JEOL Ltd. DATUM Solution Business Operations (Synthesis Example 2 and Examples 1 and 2)
Solvent: $CDCl_3$ (Example 1) and $(CD_3)_2SO$ (Synthesis examples 1 and 2 and Example 2)
Reference: $CHCl_3$ (7.26 ppm) (Example 1)
Tetramethylsilane (0.00 ppm) (Synthesis Examples 1 and 2 and Example 2)
(3) Spin Coater
Apparatus: 1H-D7, manufactured by MIKASA CO., LTD.
(4) Dryer
Apparatus: ISUZU-SVK-10S, manufactured by Isuzu Seisakusho Co., Ltd.
(5) X-Ray Photoelectron Spectroscopy (XPS)
Apparatus: ESCA 5800, manufactured by ULVAC-PHI, INCORPORATED Measurement conditions: 14.0 kV, 14 mA
Neutralization condition: Bias (V) 6.00
Extractor (V) 30
X=19.5
Y; Determined based on angles
Abbreviations represent the following meanings.
4DMA: Poly(ethylene glycol)dimethacrylate (the number of ethylene oxides≈4) [BLEMMER (registered trademark) PDE-200, manufactured by NOF CORPORATION]
ACVA: 4,4'-azobis(4-cyanovaleric acid) [V-501, manufactured by Wako Pure Chemical Industries, Ltd.]
NHS: N-hydroxysuccinimide [manufactured by Wako Pure Chemical Industries, Ltd.]
DCC: Dicyclohexylcarbodiimide [manufactured by Tokyo Chemical Industry Co., Ltd.]
BAHA: 6-[(+)-biotinamide]hexylamine
PMMA: Poly(methyl methacrylate) [weight average molecular weight: 315,000, manufactured by Polymer Source, Inc.]
IPA: 2-Propanol
DMF: N,N-dimethylformamide
PGME: Propylene glycol monomethyl ether
THF: Tetrahydrofuran Synthesis Example 1

Production of Highly Branched Polymer 1 having Carboxy Groups at its Terminal Using 4DMA and ACVA Into a 200 mL reaction flask, 53 g of PGME was charged and nitrogen was flown into the flask for 5 minutes with stirring, followed by heating until the internal liquid was refluxed (about 120° C.).

Into another 100 mL reaction flask, 6.6 g (20 mmol) of 4DMA, 2.8 g (10 mmol) of ACVA, and 53 g of PGME were charged and the atmosphere in the flask was replaced with nitrogen by charging nitrogen for 5 minutes with stirring, followed by cooling the mixture to 0° C. using an ice bath.

Into PGME refluxed in the 200 mL reaction flask, the content in the 100 mL reaction flask in which 4DMA and ACVA were charged was added dropwise over 30 minutes using a dropping pump. After completion of the dropwise addition, the obtained reaction solution was further stirred for 1 hour.

Subsequently, about 80% (86 g) of charged PGME was removed from the reaction liquid by distillation using a rotary evaporator and thereafter, the reaction liquid was added to 297 g of cold water to precipitate a polymer as a viscous product. The viscous product was isolated by decantation and redissolved in 20 g of methanol. This solution was added to 297 g of cold water and the polymer was precipitated again as a viscous product. The viscous product was isolated by decantation and redissolved in 20 g of methanol. Thereafter, the solvent was removed by distillation under reduced pressure and the residue was dried under vacuum to obtain 4.5 g of the target product (Highly branched polymer 1) as white powder.

The obtained target product had a weight average molecular weight Mw measured by GPC in terms of polystyrene of 4,200 and a degree of distribution: Mw (weight average molecular weight)/Mn (number average molecular weight) of 2.2. The number of carboxy groups in one molecule of the target product determined by neutralization titration using a sodium hydroxide aqueous solution was 5. The measurement result of $^1$H NMR spectrum of the target product is shown in FIG. 1.

Synthesis Example 2

Production of BAHA

Into a 50 mL reaction flask, 1.0 g of biotin [manufactured by Wako Pure Chemical Industries, Ltd.], 0.59 g of NHS, and 19 g of DMF were charged and the mixture was dissolved with stirring at 50° C. To this solution, 1.0 g of DCC was added and the resultant reaction liquid was stirred at 50° C. for 24 hours in a nitrogen atmosphere. Subsequently, insoluble substances were removed from the reaction liquid by filtration and then DMF was removed by distillation. The obtained residue was washed with 3 g of diethyl ether and then recrystallized with 15 g of IPA. The obtained white crystal was filtered under reduced pressure and dried under vacuum to obtain 1.0 g of biotin N-hydroxysuccinimide ester.

Figure 2:
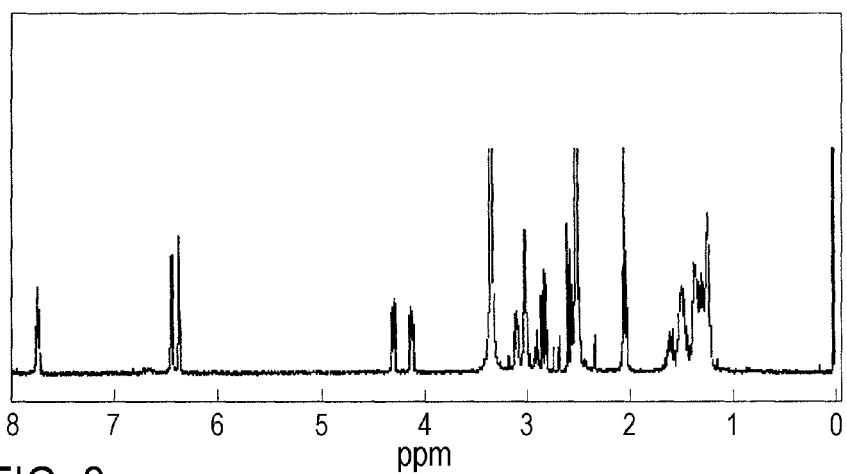
FIG. 2 is a chart showing the $^1$H NMR spectrum of 6-[(+)-biotinamide]hexylamine (BAHA) produced in Synthesis Example 2.

A solution prepared by dissolving 1.0 g of this ester in 24 g of DMF was added dropwise to a solution prepared by dissolving 2.4 g of hexamethylenediamine [manufactured by Wako Pure Chemical Industries, Ltd.] in 10 g of DMF over 40 minutes using a dropping funnel. After completion of the dropwise addition, the reaction liquid was further stirred for 18 hours. Subsequently, DMF was removed from the reaction liquid by distillation. The obtained residue was washed with 10 g of ethanol and dried under vacuum to obtain 0.82 g of the target product (BAHA) as white powder. The measurement result of $^1$H NMR spectrum of the target product is shown in FIG. 2.

Example 1

Production of Highly Branched Polymer 2 having Hydroxysuccinimide Ester at its Terminal Into a 25 mL reaction flask, 0.40 g of Highly branched polymer 1 obtained in Synthesis Example 1, 0.11 g of NHS, and 6 g of DMF were charged and the mixture was dissolved with stirring. To this solution, 0.20 g of DCC was added and the resultant reaction liquid was stirred at room temperature (about 25° C.) for 40 hours in a nitrogen atmosphere.

Subsequently, insoluble substances were removed from the reaction liquid by filtration and then DMF was removed by distillation. The obtained residue was dissolved in 4.5 g of chloroform and this solution was added to 30 g of diethyl ether. The precipitated viscous product was isolated by decantation and redissolved in 3.5 g of chloroform. Thereafter, the solvent was removed by distillation under reduced pressure and the residue was dried under vacuum to obtain 0.38 g of the target product (Highly branched polymer 2: activated carboxy group-containing highly branched polymer) as white powder.

Figure 3:
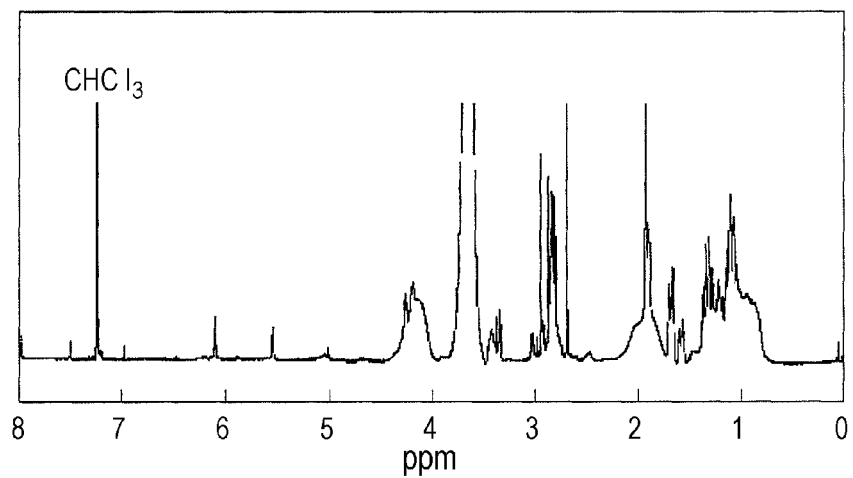
FIG. 3 is a chart showing the $^1$H NMR spectrum of Highly branched polymer 2 produced in Example 1.

A weight average molecular weight Mw of the target product measured by GPC in terms of polystyrene was not able to be measured due to decomposition of the activated ester part of the target product during the measurement. The measurement result of $^1$H NMR spectrum of the target product is shown in FIG. 3.

Example 2

Production of Highly Branched Polymer 3 having Biotin at its Terminal

Into a 25 mL reaction flask, 0.19 g of Highly branched polymer 2 obtained in Example 1 and 2 g of THF were charged to prepare a highly branched polymer solution.

Into another 50 mL reaction flask, 0.13 g of BAHA obtained in Synthesis Example 2 and 11 g of methanol were charged and the mixture was dissolved with stirring at 60° C. To this solution, the highly branched polymer solution was added and the resultant reaction liquid was stirred at room temperature (about 25° C.) for 18 hours in a nitrogen atmosphere.

Subsequently, the solvent of the reaction liquid was removed using a rotary evaporator and the residue was dried. The residue was dissolved in 4 g of methanol and a polymer was precipitated in a slurry state by adding the solution to 36 g of diethyl ether. This slurry was filtered under reduced pressure and the residue was redissolved in 4 g of methanol, followed by precipitating the polymer in the slurry state by adding the solution to 36 g of diethyl ether. This slurry was filtered under reduced pressure and the residue was dried under vacuum to obtain 0.09 g of the target product (Highly branched polymer 3; biomolecule-compatible highly branched polymer) as white powder.

Figure 4:
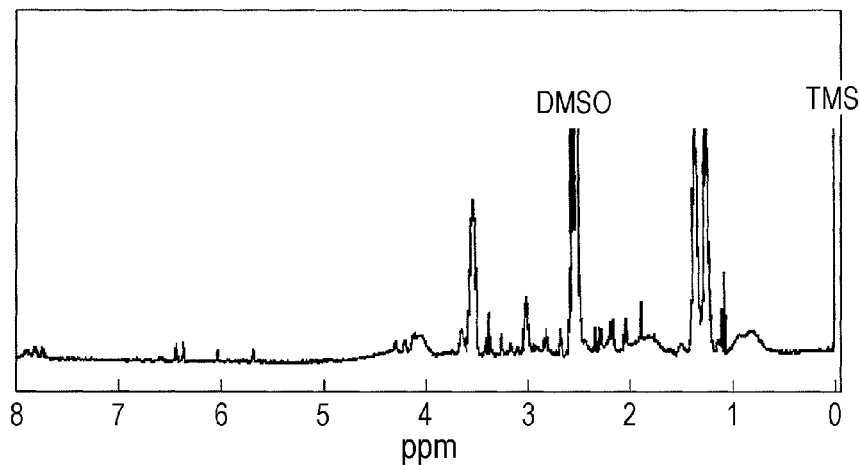
FIG. 4 is a chart showing the $^1$H NMR spectrum of Highly branched polymer 3 produced in Example 2.

A weight average molecular weight Mw of the target product measured by GPC in terms of polystyrene was not able to be measured due to low solubility of the target product in a solvent. The measurement result of $^1$H NMR spectrum of the target product is shown in FIG. 4.

Example 3

Fabrication of Molecular-Recognition Film using Highly Branched Polymer 3

Highly branched polymer 3 obtained in Example 2 was dissolved in THF-methanol mixed solution (mass ratio 9:1) so that the concentration of Highly branched polymer 3 is 1% by mass and the solution was filtered to prepare a varnish. This varnish was applied onto a silicon wafer by spin coating (3,000 rpm×60 seconds). The applied film was dried at room temperature (about 25° C.) for 24 hours under vacuum to remove the solvent, and whereby a molecular-recognition film was obtained.

Examples 4

Fabrication of Molecular-Recognition Film using Highly Branched Polymer 3 and PMMA 1

Figure 5:
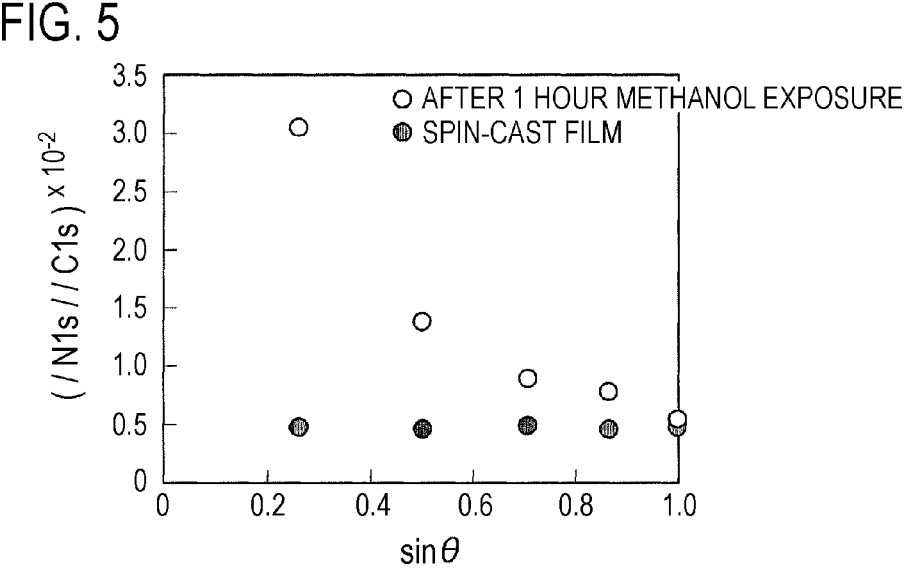
FIG. 5 is a graph showing the result of surface composition analysis (an intensity ratio ($I_{N1s}/I_{c1s}$)) of nitrogen atoms to carbon atoms against sin θ (θ: the emission angle of photoelectrons) by angle-resolved XPS measurement of molecular-recognition films fabricated in Example 4 and Example 5.

Highly branched polymer 3 obtained in Example 2 and PMMA were mixed in a mass ratio of 2:8. This mixture was dissolved in THF-methanol mixed solution (mass ratio 9:1) so that the concentration of the mixture is 1% by mass and the solution was filtered to prepare a varnish. This varnish was applied onto a silicon wafer by spin coating (3,000 rpm×60 seconds). The applied film was dried at room temperature (about 25° C.) for 24 hours under vacuum to remove the solvent, and whereby a molecular-recognition film was obtained. The surface composition of the obtained film was evaluated based on angle-resolved XPS measurement. The result is shown in FIG. 5.

Examples 5

Fabrication of Molecular-Recognition Film using Highly Branched Polymer 3 and PMMA 2

The film obtained in Example 4 was placed in a desiccator having a capacity of about 50 mL in which a beaker containing 5 mL of methanol was placed to carrying out solvent annealing treatment at room temperature (about 25° C.) for 1 hour. After drying, angle-resolved XPS measurement was carried out to the obtained film to evaluate the surface composition of the film indicated by an intensity ratio of carbon atoms and nitrogen atoms as a function of sin θ (θ: the emission angle of photoelectrons). The result is also shown in FIG. 5. As the value of sin θ is smaller, the intensity ratio indicates an intensity ratio closer to the film surface.

As shown in FIG. 5, by carrying out the solvent annealing treatment with methanol for 1 hour, a ratio of nitrogen atoms to carbon atoms was increased close to the film surface. In other words, it was ascertained that more highly branched polymers 3 having biotin at its terminals containing nitrogen atoms existed close to the surface.

Example 6

Recognition of Streptavidin by Molecular-Recognition Film

The molecular-recognition film obtained in Example 5 was immersed in 50 μmol/L of a streptavidin [manufactured by Wako Pure Chemical Industries, Ltd.]/phosphate buffered saline (PBS) solution having a pH of 7.3 at room temperature (about 25° C.) for 15 minutes. A film obtained from this molecular-recognition film by washing with water and drying and a film before immersing into the streptavidin solution were subjected to XPS measurement and the surface compositions of the films were evaluated. The results are shown in FIG. 6 (before immersion) and FIG. 7 (after immersion).

Figure 6:
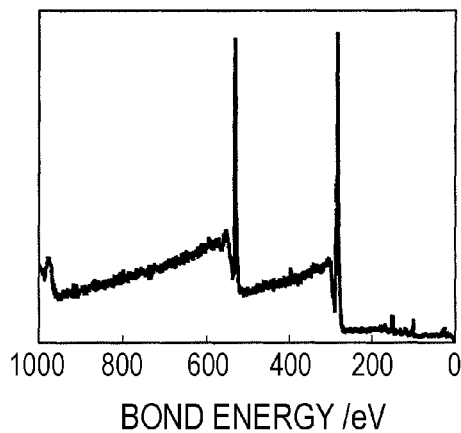
FIG. 6 is a chart showing the result of surface composition analysis of a molecular-recognition film before immersing into a streptavidin solution used in Example 6 by XPS measurement.
Figure 7:
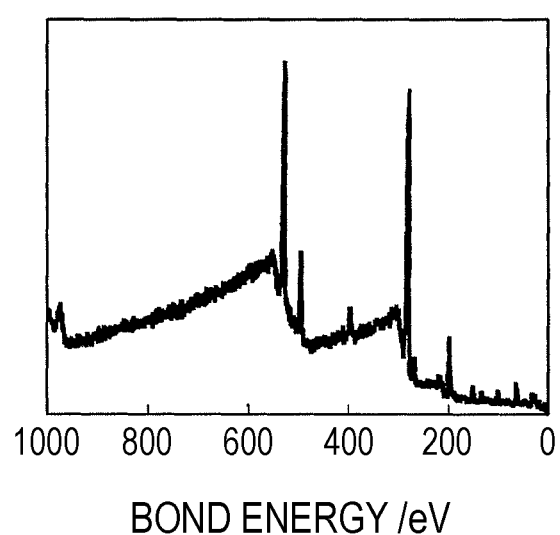
FIG. 7 is a chart showing the result of surface composition analysis of a molecular-recognition film after immersing into a streptavidin solution fabricated in Example 6 by XPS measurement.

As shown in FIGS. 6 and 7, the increase in the peak (around 398 eV) of nitrogen atoms ($N_{1s}$) after immersion caused by streptavidin was observed in comparison with the peak of the film before immersion. From this result, fixation (recognition) of streptavidin at the surface of the molecular-recognition film was ascertained.

The invention claimed is:

1. A biomolecule-compatible highly branched polymer obtained by polymerizing a monomer having an alkylene oxide and two or more radically polymerizable double bonds in a molecule in the presence of a polymerization initiator in an amount of 5 mol % or more and 200 mol % or less relative to the number of moles of the monomer, wherein
molecular terminals of the biomolecule-compatible highly branched polymer have one biomolecular site of at least one pair selected from the group consisting of the pairs of combinations of biotin and avidin, an antigen and an antibody, a polynucleotide and a polynucleotide having a complementary base sequence of the former polynucleotide, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

2. The biomolecule-compatible highly branched polymer according to claim 1, wherein
the monomer is a compound having either or both of a vinyl group and a (meth)acrylic group.

3. The biomolecule-compatible highly branched polymer according to claim 2, wherein
the monomer is a divinyl compound or a di(meth)acrylate compound.

4. The biomolecule-compatible highly branched polymer according to claim 3, wherein
the monomer is a compound of Formula [1]:

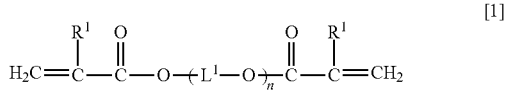

(where $R^1$ each is independently a hydrogen atom or a methyl group; $L^1$ is a $C_{2-6}$ alkylene group; and n is an integer of 1 to 30).

5. The biomolecule-compatible highly branched polymer according to claim 1, wherein
the polymerization initiator is an azo-based polymerization initiator.

6. The biomolecule-compatible highly branched polymer according to claim 5, wherein
the polymerization initiator is 4,4'-azobis(4-cyanovaleric acid).

7. A varnish comprising:
the biomolecule-compatible highly branched polymer as claimed in claim 1.

8. A thin film fabricated from the biomolecule-compatible highly branched polymer as claimed in claim 1.

9. A resin blend comprising:
(a) the biomolecule-compatible highly branched polymer as claimed in claim 1; and
(b) a low hydrophilic thermoplastic resin.

10. A thin film fabricated from the resin blend as claimed in claim 9.

11. A method for producing a thin film fabricated from the biomolecule-compatible highly branched polymer as claimed in claim 1, the method comprising:
applying a liquid in which the biomolecule-compatible highly branched polymer is contained in a solvent onto a substrate by a spin coating method to form a coating film; and
removing the solvent by drying the coating film.

12. A method for producing a thin film fabricated from the resin blend as claimed in claim 9, the method comprising:
applying a liquid in which the resin blend is contained in a solvent onto a substrate by a spin coating method to form a coating film;
removing the solvent by drying the coating film; and
annealing the obtained coating film in the atmosphere of a hydrophilic medium.

13. A molecular-recognition surface chip comprising:
the thin film as claimed in claim 11 on a substrate, wherein
with the thin film, the molecular-recognition surface chip is capable of recognizing one biomolecule of at least one pair selected from the group consisting of the pairs of combinations of biotin and avidin, an antigen and an antibody, a polynucleotide and a polynucleotide having a complementary base sequence of the former nucleotide, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

14. An activated carboxy group-containing highly branched polymer obtained by causing a carboxy group-containing highly branched polymer obtained by polymerizing a monomer having an alkylene oxide and two or more radically polymerizable double bonds in a molecule, in the presence of a polymerization initiator having carboxy groups in the molecule of the polymerization initiator in an amount of 5 mol % or more and 200 mol % or less relative to the number of moles of the monomer, to react with N-hydroxysuccinimide wherein a part of or all of the carboxy groups are hydroxysuccinimide-esterified.

15. A method for producing the biomolecule-compatible highly branched polymer as claimed in claim 1, the method comprising:

causing an activated carboxy group-containing highly branched polymer obtained by causing a carboxy group-containing highly branched polymer obtained by polymerizing a monomer having an alkylene oxide and two or more radically polymerizable double bonds in a molecule, in the presence of a polymerization initiator having carboxy groups in the molecule of the polymerization initiator in an amount of 5 mol % or more and 200 mol % or less relative to the number of moles of the monomer, to react with N-hydroxysuccinimide wherein a part of or all of the carboxy groups are hydroxysuccinimide-esterified to react with a compound having a functional group capable of reacting with the activated carboxy group and having one biomolecular site of at least one pair selected from the group consisting of the pairs of combinations of biotin and avidin, an antigen and an antibody, a polynucleotide and a polynucleotide having a complementary base sequence of the former nucleotide, cDNA and mRNA, an enzyme (an active site) and a substrate, an enzyme (an active site) and a product, an enzyme (an active site) and a competitive inhibitor, an enzyme (a coenzyme binding site) and a coenzyme, an enzyme (a coenzyme binding site) and a triazine dye, protease and a protease inhibitor, a Fc site and protein A, a Fc site and protein G, lectin and a sugar, a hormone receptor and a hormone, DNA and a DNA binding protein, heparin and fibronectin, and heparin and laminin.

16. The method according to claim 15, wherein the functional group capable of reacting with the activated carboxy group is an amino group.

\* \* \* \* \*